US012721930B2

(12) United States Patent
Nam et al.

(10) Patent No.: US 12,721,930 B2
(45) Date of Patent: Sep. 1, 2026

(54) DECELLULARIZED NERVE GRAFT AND METHOD OF MANUFACTURING THE SAME

(71) Applicant: L&C Bio Co., Ltd., Gyeonggi-do (KR)

(72) Inventors: Dong Hyun Nam, Seoul (KR); Sang Chul Kim, Seoul (KR); Kee Won Lee, Seoul (KR); Hyung Gu Kim, Seoul (KR); Whan Chul Lee, Seoul (KR)

(73) Assignee: L&C Bio Co., Ltd., Gyeonggi-do (KR)

( * ) Notice: Subject to any disclaimer, the term of this patent is extended or adjusted under 35 U.S.C. 154(b) by 886 days.

(21) Appl. No.: 17/791,113

(22) PCT Filed: Dec. 21, 2020

(86) PCT No.: PCT/KR2020/018767
§ 371 (c)(1),
(2) Date: Jul. 6, 2022

(87) PCT Pub. No.: WO2022/138992
PCT Pub. Date: Jun. 30, 2022

(65) Prior Publication Data

US 2023/0041245 A1 Feb. 9, 2023

(51) Int. Cl.
*A61L 27/36* (2006.01)
*C12N 5/071* (2010.01)

(52) U.S. Cl.
CPC ........ *A61L 27/3687* (2013.01); *C12N 5/0697* (2013.01); *A61L 2430/32* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 10,293,082 | B2 | 5/2019 | Sierad et al. |
| 10,814,037 | B2 | 10/2020 | Sun et al. |

FOREIGN PATENT DOCUMENTS

| | | | |
|---|---|---|---|
| CN | 106139250 | A | 11/2016 |
| CN | 106913907 | A | 7/2017 |
| CN | 108465126 | A | 8/2018 |
| CN | 109621008 | A | 4/2019 |
| CN | 109701077 | A | 5/2019 |
| KR | 20180003879 | A | 1/2018 |

OTHER PUBLICATIONS

Wüthrich et al. (Materials Science and Engineering: C 117 (published online: Aug. 2020): 111311.) (Year: 2020).*

ResearchGate_NaOH (https://www.researchgate.net/post/How-to-change-the-pH-of-PBS-to-pH9-and-pH11, accessed: Apr. 25, 2025) (Year: 2025).*

Moore (Current Protocols in Molecular Biology 35.1 (1996): A-2.) (Year: 1996).*

Price et al. (Tissue Engineering Part C: Methods 21.1 (2015): 94-103.) (Year: 2015).*

Choudhury et al. (Acta biomaterialia 115 (published online: Aug. 2020): 51-59.) (Year: 2020).*

Kajbafzadeh et al. (Tissue Engineering Part C: Methods 19.8 (2013): 642-651.) (Year: 2013).*

Willemse et al. (Materials Science and Engineering C 108 (Published online: Sep. 2019)) (Year: 2019).*

McCrary et al. (Tissue Engineering Part C: Methods 26.1 (Published Online: Jan. 2020): 23-36.) (Year: 2020).*

Hudson et al. (Tissue engineering 10.9-10 (2004): 1346-1358.) (Year: 2004).*

Chemical book website (https://m.chemicalbook.com, Sodium deoxycholate CAS#: 302-95-4, accessed Jan. 26, 2026, hereinafter Chem (Year: 2026).*

Sigma-Aldrich, Product Information, Sodium deoxycholate monohydrate (Year: 2017).*

“Acid-Base Equilibria”, https://christou.chem.ufl.edu/wp-content/uploads/sites/62/2017/01/Chapter-18-Acids-and-Bases-Week-1.pdf, accessed: Jan. 27, 2026 (Year: 2026).*

Garcia-Perez, MM., et al. “A modified chemical protocol of decellularization of rat sciatic nerve and its recellularization with mesenchymal differentiated Schwann-Like cells: Morphological and functional assessments”, Histology and Histopathology, (2017) 32: 779-792.

Kefeng, Dou et al., “Xenotransplantation”, People’s Military Medical Press, Beijing, 2013, including English translation, 4 pages.

* cited by examiner

*Primary Examiner* — Maria G Leavitt
*Assistant Examiner* — Brendan Thomas Tinsley
(74) *Attorney, Agent, or Firm* — McNeill PLLC

(57) ABSTRACT

The present invention relates to a decellularized nerve graft using allogeneic and heterologous nervous tissues and a method of manufacturing the same.

In the present invention, by using a low-concentration basic solution and a surfactant as a decellularization solution, cell and tissue toxicity caused by a solvent or surfactant remaining in the tissue may be minimized by minimizing the use of a basic solution and an anionic surfactant in the entire manufacturing process. In addition, a peristaltic pump may be used to maintain the tissue structure and effectively remove lipid and cells.

9 Claims, 6 Drawing Sheets

[Fig 1]
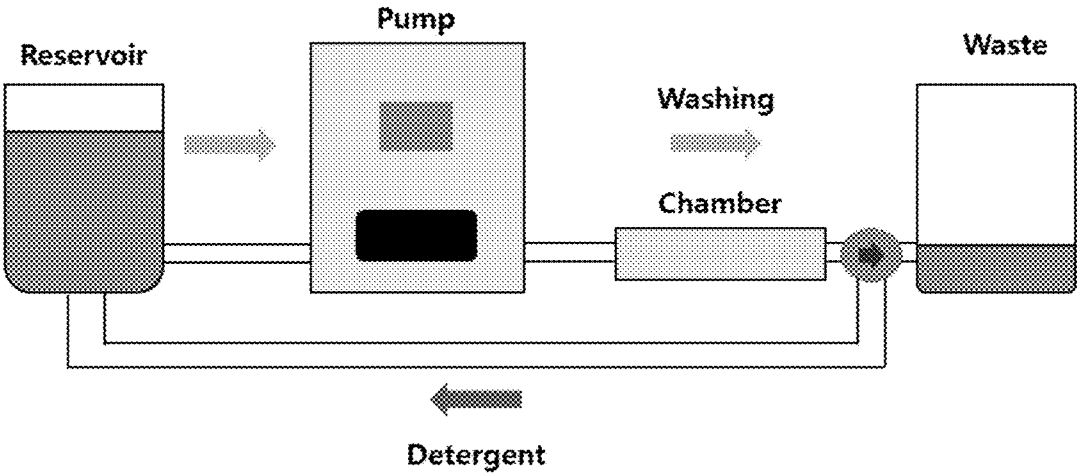
[Fig 2A]
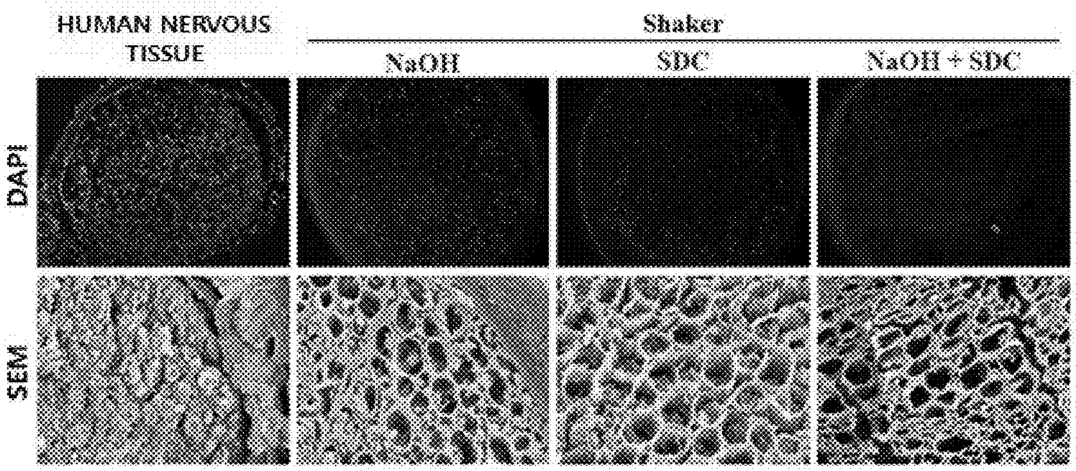

[Fig 2B]
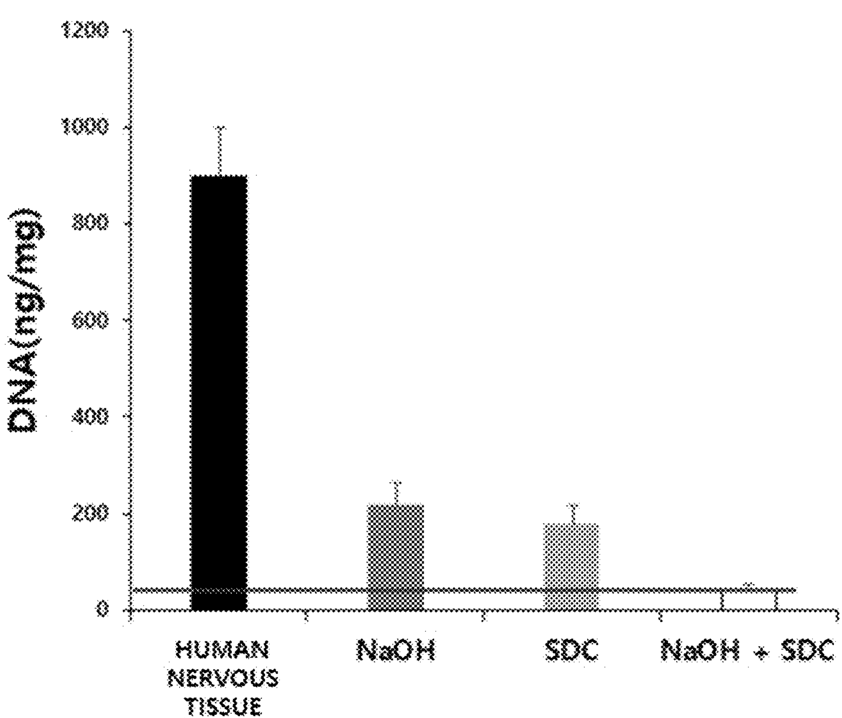
[Fig 3A]
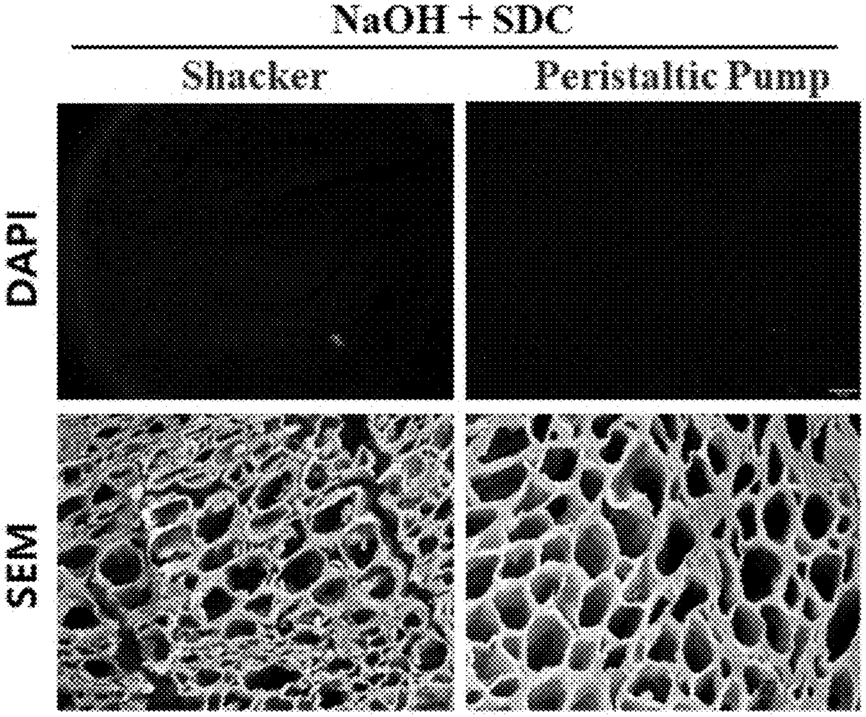

[Fig 3B]
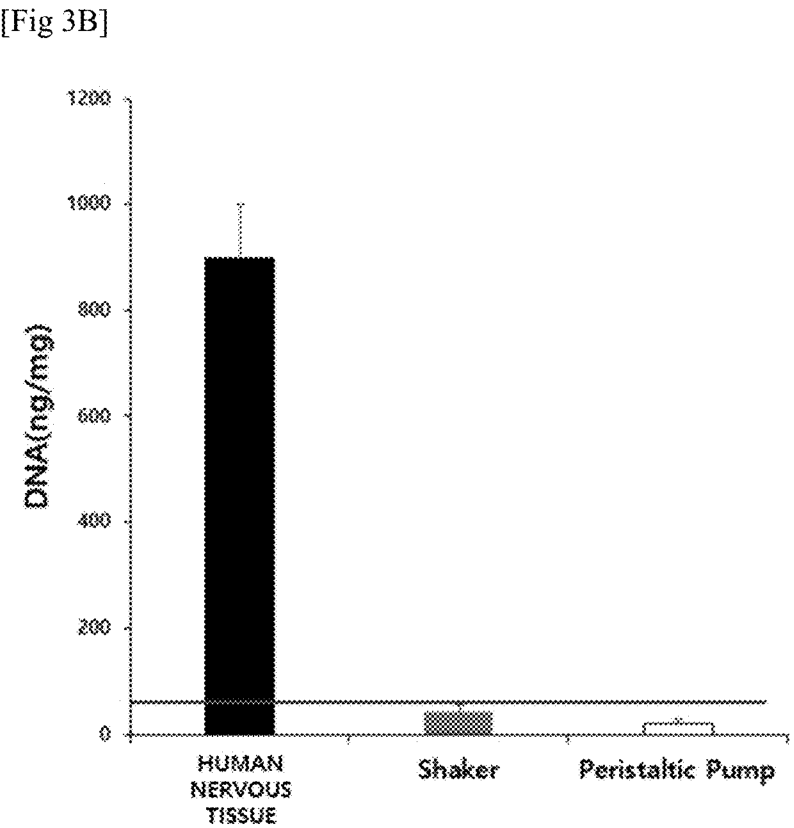
[Fig 3C]
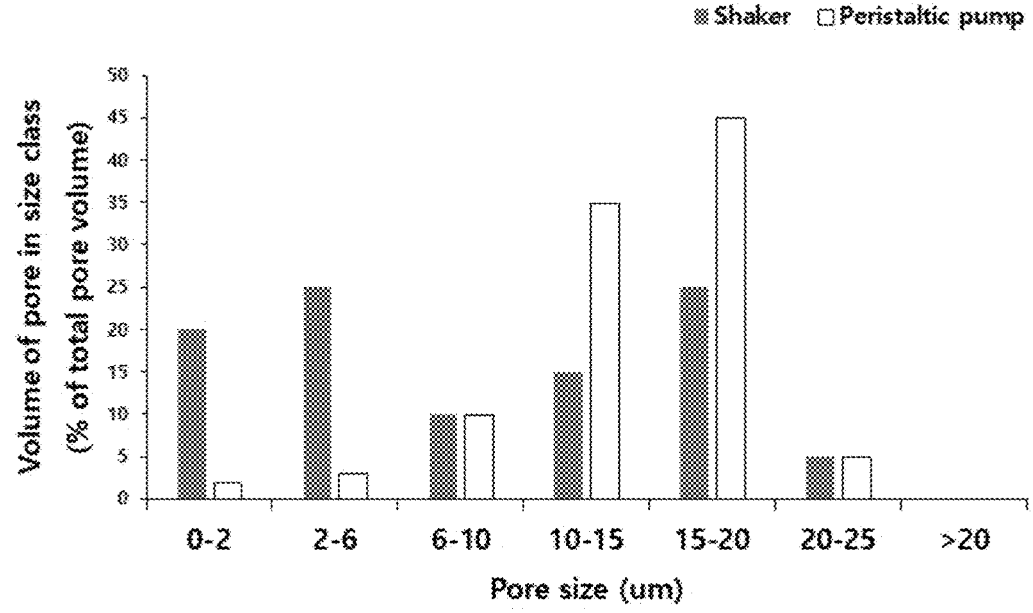

[Fig 4]
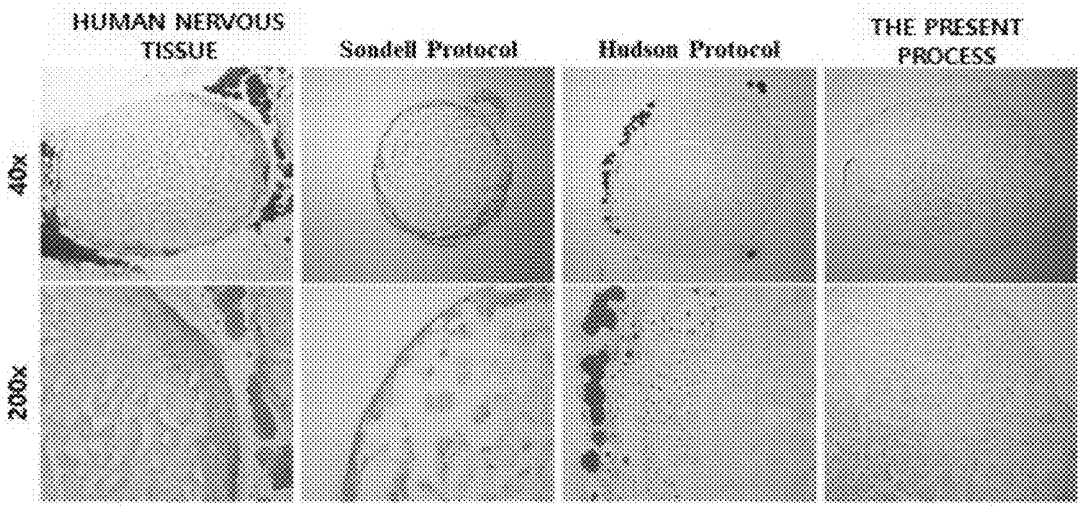
[Fig 5A]
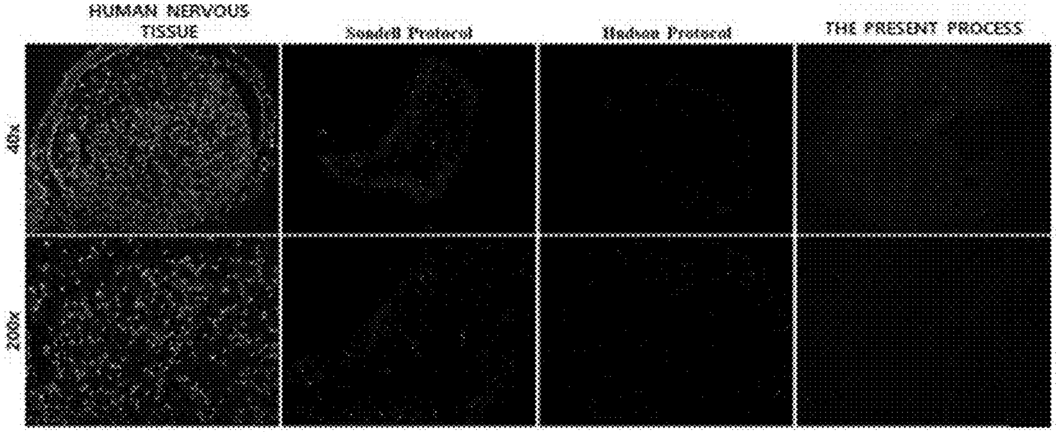

[Fig 5B]
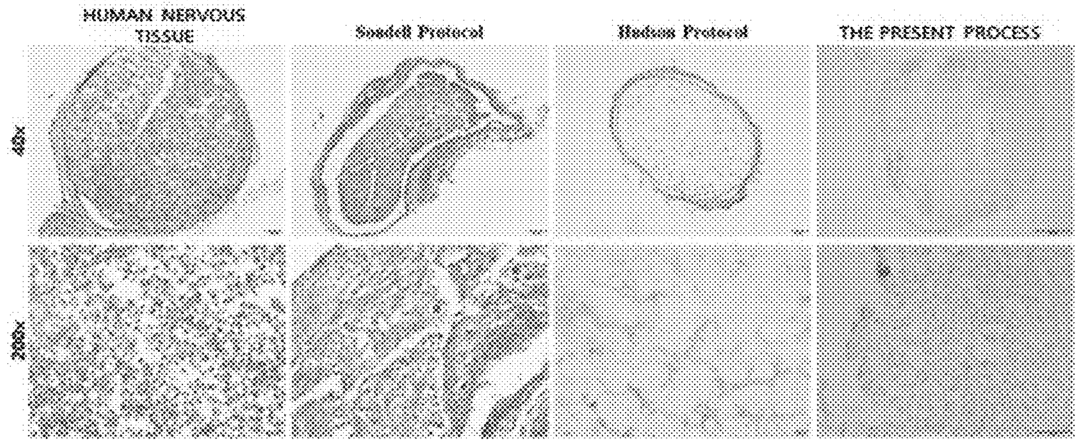
[Fig 5C]
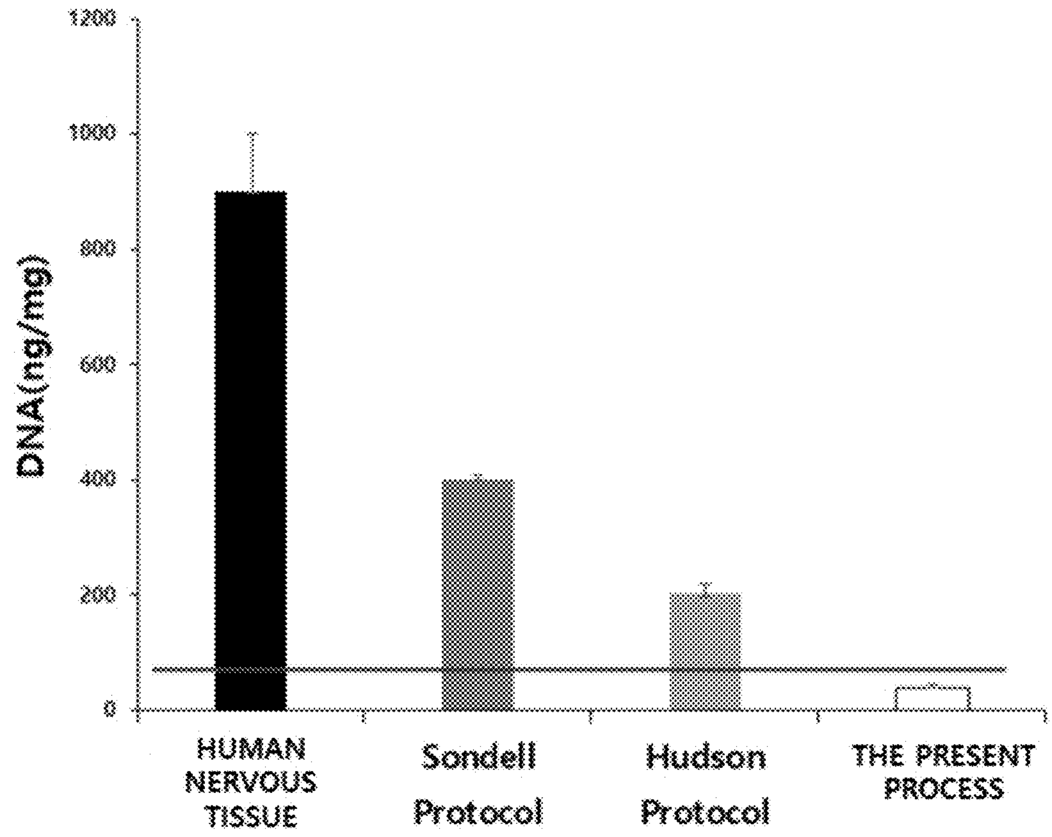

[Fig 5D]
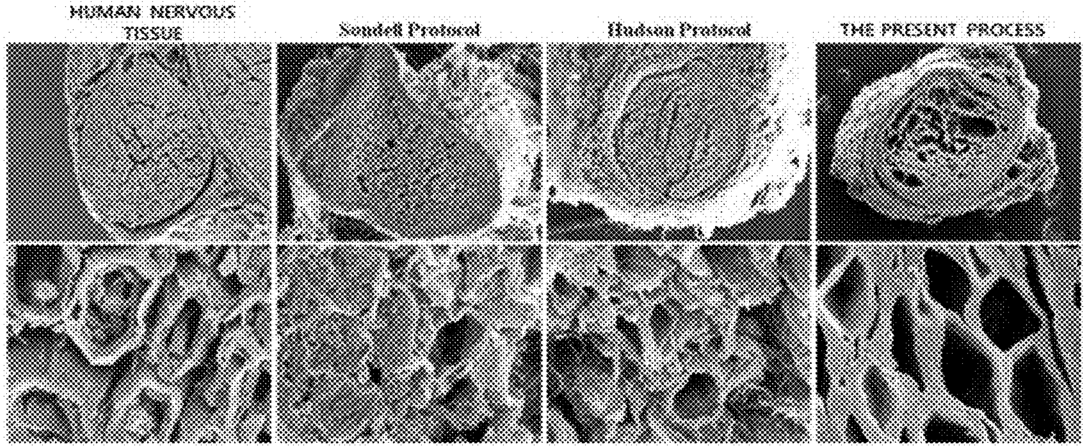
[Fig 6]
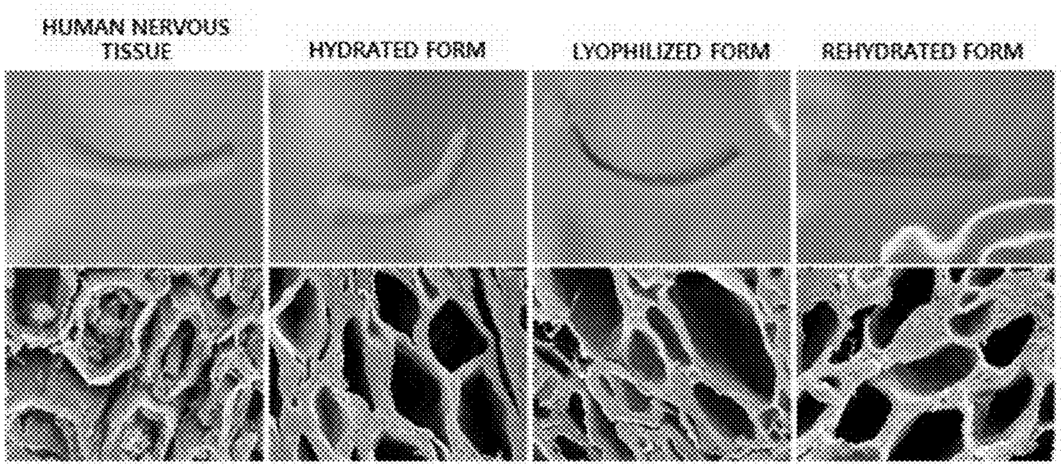

DECELLULARIZED NERVE GRAFT AND METHOD OF MANUFACTURING THE SAME

CROSS-REFERENCE TO RELATED APPLICATIONS

This application is a national phase entry pursuant to 35 U.S.C. § 371 of International Application No. PCT/KR2020/018767, filed Dec. 21, 2020, which is incorporated by reference herein in its entirety for any purpose.

TECHNICAL FIELD

The present invention relates to decellularized nerve grafts using allogeneic and heterologous nervous tissues and a method of manufacturing the same.

TECHNICAL FIELD

When a peripheral nerve is damaged due to acquired factors, that is, when a nerve is damaged by trauma or surgically removed for treatment, peripheral nerve regeneration procedures are used to connect the damaged or removed nerves. However, it is not easy to restore a nerve that has been cut once, and even with surgery, in most cases, it is almost impossible to accurately connect the nerve, and even when a nerve is connected, regeneration is not performed well due to the difference in tension. To this end, regeneration is performed using a graft such as autologous or artificial nerves.

In the case of autologous nerve transplantation, since a patient's nerve is transplanted, it has a low risk of immune response and exhibits excellent nerve regeneration. On the other hand, the autologous nerve transplantation has disadvantages in that it is difficult to obtain a sufficient amount of nervous tissue, a collectable area is limited, it is difficult to obtain nervous tissue consistent with the thickness and shape of the damaged area, and there is a high risk of complications such as the loss of motor and sensory abilities.

In the case of artificial nerve transplantation, an artificial nerve conduit made using an absorbable material such as polyglycolic acid (PGA) or type I collagen in the form of a nervous conduit is used. The manufacture of an artificial nerve conduit can form a desired size of nerve but has a disadvantage of being limitedly used only for the regeneration of 3-cm or smaller sensory nerves since there is a risk of an immune response and the lack of nerve regeneration ability.

As a method for overcoming the above disadvantages, allogeneic nerve transplantation, which uses nerves donated from the same species after decellularization, is used. Since allogeneic nerve transplantation is to transplant allogeneic nerves, tissue decellularization is essential, and it has advantages in that the decellularized nerve has a low risk of an immune response, and various sizes of nerves are produced to be used in necessary areas.

In the case of an allogeneic nerve graft, cells are removed to minimize an immune response caused by cells remaining in tissue, and generally, a method of selectively removing only cells without damage to tissue using a difference in physicochemical characteristics between the cells and the extracellular matrix is used. In addition, since the immune response is mainly caused by a membrane protein present in the cell membrane, cells are removed using a protease for removing a membrane protein and various surfactants for removing phospholipids, which are the main components of the cell membrane. Generally, an ionic surfactant such as sodium dodecyl sulfate (SDS), or a non-ionic surfactant such as Triton™ X-100, Tween® 20, Tween® 40, Tween® 60, Tween® 80, Nonidet® P-10 (NP-10) or Nonidet®-40 (NP-40) is used. However, a decellularization method using a commonly used enzyme and surfactant may damage the structure of nervous tissue and may cause cell and tissue toxicity in the body due to their residue. In addition, to minimize this, there is a disadvantage in that large amounts of time and cost for washing has to be input.

There are two currently known methods for removing cells in nervous tissue, such as the Sondell method and the Hudson method. The Sondell method uses Triton™ X-100 and sodium deoxycholate (SDC), and the Hudson method uses sulfobetaine and SDC. However, these methods are disadvantageous in that they can damage the structure of nervous tissue because a high concentration of surfactant or enzyme is treated for a long time and all processes are performed using a shaker, and it takes a lot of time to remove the surfactant remaining in the tissue and replace a solution, so 3 to 4 days are needed to complete the processes.

Currently, technology for decellularizing nervous tissue has been developed in Korea, but it is known that no products have been mass-produced. On the other hand, Avance (Axogen, U.S.A.) is a product in which cells have been removed by an improved Hudson method and is currently the only decellularized human nerve graft that is reported to be effective in regenerating peripheral nerves damaged by trauma. However, Avance employs enzymes and surfactants at high ratios and may cause immune responses due to residual enzymes and surfactants in tissue, and requires a huge amount of washing time to minimize the reactions, so its manufacturing process takes a long time, and since all processes are carried out with a shaker, the tissue can be damaged. In addition, since Avance is provided only in a frozen state, it is difficult to distribute or store it.

Therefore, the inventors intend to suggest a decellularized nerve graft that can be transplanted into a peripheral nerve-damaged patient through novel decellularization technology and a method of manufacturing the same.

RELATED ART DOCUMENT

Non-Patent Document

1. Histol Histopathol (2017) 32: 779-792

DISCLOSURE

Technical Problem

The present invention is directed at providing a decellularized nerve graft that can be transplanted into a peripheral nerve-damaged patient through novel decellularization technology and a method of manufacturing the same.

More specifically, the present invention provides a decellularized nerve graft that uses a low-concentration basic solution and an anionic surfactant as a decellularization solution to improve the disadvantages of the collapse of the structure of the graft when a high-concentration basic or a surfactant solution as a decellularization solution are used and incomplete removal of cells when a low-concentration basic solution or a surfactant is used as a decellularization solution, and minimizes cell and tissue toxicity caused by a solvent or surfactant remaining in the tissue and reduces the time for washing by minimizing the use of a basic solution and an anionic surfactant in the entire manufacturing process, and a method of manufacturing the same.

In addition, the present invention provides, to improve disadvantages in that cells are not completely removed and the structure of tissue may be damaged in the decellularization process performed using a shaker, decellularized nerve grafts in lyophilized and hydrated forms, which can maintain the structure of tissue and effectively remove lipids and cells using a peristaltic pump and be stored at room temperature, in addition to frozen storage, and a method of manufacturing the same may be provided.

Technical Solution

The present invention provides a method of manufacturing a decellularized nerve graft, which includes:

a) removing a lipid component of nervous tissue; and b) removing cells from the lipid component-removed nervous tissue, wherein, in b), the nervous tissue is treated with a basic solution and an anionic surfactant, and a) and b) are performed using a peristaltic pump system.

In addition, the present invention provides a decellularized nerve graft manufactured by the above-described manufacturing method.

Advantageous Effects

In the present invention, decellularization and delipidation processes, which exclude the use of an enzyme, use a low-concentration basic solution and an anionic surfactant as a decellularization solution, so the basic solution and the anionic surfactant can be used in an amount as small as possible to minimize cell and tissue toxicity caused by the residual surfactant. In addition, the present invention can be used to solve problems when the basic solution or surfactant is used alone, for example, in the case of using a high concentration thereof, a problem that the structure collapses can be solved, and in the case of using a low concentration thereof, a problem that cells are not completely removed can be solved. In addition, the present invention can completely remove cells while maintaining the structure of nervous tissue.

In addition, in the present invention, unlike the conventional process, adipose tissue can be effectively removed by further performing delipidation as well as decellularization.

In addition, while the conventional process is performed using a shaker, which collapses the structure of a graft, in the present invention, the present invention, a process is performed using a peristaltic pump to uniformly maintain the structure of tissue and effectively perform decellularization of the tissue. In addition, the conventional process takes usually 4 to 5 days to manufacture a decellularized nerve graft, whereas the period of delipidation and decellularization can be shortened to 2 days according to the method of the present invention.

In addition, unlike conventional products distributed in a frozen state, the present invention can provide a lyophilized or hydrated decellularized nerve graft that can be stored at room temperature.

DESCRIPTION OF DRAWINGS

FIG. 1 is a schematic diagram illustrating the process of manufacturing a decellularized nerve graft using a peristaltic pump.

FIG. 2 shows a set of DAPI and SEM images showing the decellularization degree and structure of nervous tissue according to a decellularization condition (FIG. 2A) and a DNA quantification graph (FIG. 2B).

FIG. 3 shows a set of DAPI and SEM images showing the decellularized degree and structure of nervous tissue according to the use of a peristaltic pump (FIG. 3A), a DNA quantification graph (FIG. 3B), and a graph showing the uniformity of tissue (FIG. 3C ).

FIG. 4 is a set of images stained with Oil Red O to confirm the delipidation of decellularized nervous tissues according to a process of the present invention.

FIG. 5 shows a set of DAPI, H&E, and SEM images (FIGS. 5A and 5B) for confirming the decellularization degree and structure of nervous cells decellularized according to a conventional process and a process of the present invention, and the DNA quantification graph (FIG. 5C). FIG. 5D shows SEM images confirming the tissue structure.

FIG. 6 are images obtained by visually observing decellularized nerve grafts in lyophilized and hydrated forms, which are manufactured according to examples of the present invention and their SEM images.

MODES OF THE INVENTION

The present invention relates to a method of manufacturing a decellularized nerve graft, which includes:

a) removing a lipid component of nervous tissue; and b) removing cells from the lipid component-removed nervous tissue, wherein, in b), the nervous tissue is treated with a basic solution and an anionic surfactant, and a) and b) are performed using a peristaltic pump system.

In one embodiment of the present invention, it was confirmed that by using a basic solution and an anionic surfactant are used as a decellularization solution, the amounts of the basic solution and anionic surfactant used are minimized and cells are completely removed while maintaining the neural structure. In addition, as a peristaltic pump is used in delipidation and decellularization processes, it was confirmed that the structure of tissue can be maintained and lipids and cells can be more effectively removed.

Hereinafter, the method of manufacturing a decellularized nerve graft according to the present invention will be described in further detail.

In the present invention, the decellularized nerve graft refers to a product that is manufactured by delipidation and decellularization of nervous tissue according to the present invention. Such a decellularized nerve graft can be transplanted into a peripheral nerve-damaged patient.

In the present invention, the nervous tissue may be allogeneic or heterologous nervous tissue. Allogeneic may mean being derived from a human, heterologous may mean being derived from an animal other than a human, for example, a mammal such as a pig, a cow, or a horse.

In the present invention, before a), washing the nervous tissue and/or trimming the nervous tissue may be further performed.

In one embodiment, a lipid may be detached from the nervous tissue using forceps.

In the present invention, a) may be a step of removing a lipid component of the nervous tissue for the delipidation of the nervous tissue. Delipidation means the removal of a lipid component from the nervous tissue.

In one embodiment, the delipidation may be performed using a delipidation solution. The delipidation solution may include a polar solvent, a non-polar solvent, or a mixed solvent thereof. As the polar solvent, water, an alcohol or a mixed solvent thereof may be used, and as the alcohol, methanol, ethanol or isopropyl alcohol may be used. In addition, as the non-polar solvent, hexane, heptane, octane or a mixed solvent thereof may be used. Specifically, in the present invention, as the delipidation solution, a mixed solution of isopropyl alcohol (IPA) and hexane may be used. Here, a mixing ratio of isopropyl alcohol and hexane may be 20:80 to 80:20.

In one embodiment, a) may be performed at 50 to 300 rpm. When a) is performed under this condition, the structure of nervous tissue is well maintained, and a delipidation effect is excellent.

The time for treatment with the delipidation solution may be 2 to 16 hours.

In the present invention, b) is a step for removing cells from the nervous tissue in which a lipid component has been removed in a), so the nervous tissue can be decellularized. Decellularization refers to the removal of other cell components other than the extracellular matrix from the nervous tissue, for example, the nucleus, the cell membrane, or nucleic acid. According to decellularization, an immune response caused by cells remaining in tissue may be inhibited during the transplantation of nervous tissue. In the present invention, the nervous tissue that has been delipidated and decellularized may be expressed as a decellularized nerve graft.

In one embodiment, the decellularization may be performed using a decellularization solution. As the decellularization solution, a basic solution and an anionic surfactant may be used.

In the present invention, the order of treatment of the basic solution and the anionic surfactant is not limited, and by a method of treating the nervous tissue with the basic solution and then with the anionic surfactant, decellularization may be performed. Alternatively, by a method of treating the nervous tissue with the anionic surfactant and then the basic solution, decellularization may be performed.

As the basic solution, one or more selected from the group consisting of sodium hydroxide, potassium hydroxide, ammonium hydroxide, calcium carbonate, magnesium hydroxide, calcium hydroxide, and ammonia may be used. In the present invention, as the decellularization solution, sodium hydroxide (NaOH) may be used.

In addition, as the anionic surfactant, one or more selected from the group consisting of sodium deoxycholate (SDC), sodium dodecyl sulfate (SDS), alkylbenzene sulfonate (ALS), alcohol ether sulfates (AES), sodium lauryl sulfate (SLS) and polyethylene glycol (PEG) may be used.

Conventionally, decellularization was performed using a surfactant or enzyme. However, when an enzyme is used, it may damage nervous tissue, and when the enzyme remains and is transplanted into the body, it may damage the original tissue of a patient, and when the damage became severe, there was a problem of causing an immune response. In addition, when a surfactant is used, a high concentration of surfactant is required, and washing is needed to minimize the residual of the surfactant, which may cause cell and tissue toxicity in the body. In addition, when the concentration is low, desired decellularization efficiency was not obtained. Therefore, in the present invention, the use of the basic solution and the anionic surfactant as a decellularization solution in decellularization may solve the above-described problem, and has the advantage of no cell toxicity.

In one embodiment, the concentration of the basic solution may be 0.1 to 8N, 0.1 to 0.5 N, or 0.1 to 2 N. In addition, the concentration of the surfactant may be 2 to 16%, 2 to 8%, or 2 to 4%. In the above concentration ranges, cell removal is easy.

In one embodiment, b) may be performed at 50 to 300 rpm. Under this condition, the structure of tissue may be maintained well, and decellularization efficiency is excellent.

In addition, in one embodiment, b) may be performed for 1 to 18 hours, 1 to 8 hours, or 2 to 4 hours. Specifically, the time for treatment with the basic solution may be 30 minutes to 9 hours, 1 to 4 hours, or 1 to 2 hours, and the time for treatment with the anionic surfactant may be 30 minutes to 9 hours, 1 to 4 hours, or 1 to 2 hours. In these time ranges, cell removal is easy.

In the present invention, a) and b), that is, the delipidation and the decellularization may be performed using a peristaltic pump system. Here, the peristaltic pump may be any peristaltic pump that is used in the art without limitation.

In the present invention, the peristaltic pump system may include a peristaltic pump;

a chamber connected with the peristaltic pump and containing nervous tissue;

a reservoir connected with the peristaltic pump and storing a treatment liquid for treating the nervous tissue; and a waste water storage bin connected with the chamber and discharging the treatment liquid that has been used for treating the nervous tissue.

That is, the peristaltic pump may be connected with each of the reservoir and the chamber. Therefore, the treatment liquid in the reservoir may move to the chamber through the peristaltic pump and react with the nervous tissue present in the chamber, followed by discharging to the waste water storage bin.

In one embodiment, the treatment liquid may include a delipidation solution, a decellularization solution, and a washing solution to be described below.

In one embodiment, the treatment liquid that has been used for treating the nervous tissue may be recycled and reused. That is, the treatment liquid that has been used for treating the nervous tissue may not be discharged to the waste water storage bin, may move to the reservoir, and move back to the chamber using a peristaltic pump. In one embodiment of the present invention, a three-way stopcock may be used as a connecting tube for connecting the chamber and the waste water storage bin to facilitate the circulation of the treatment liquid.

In the present invention, through the delipidation and decellularization processes, 1) cell toxicity occurring in the body due to a residual basic solution or surfactant may be minimized using minimal amounts of the basic solution and the surfactant, 2) immune response in the body caused by cells remaining in tissue may be minimized by effectively removing lipids and cells while maintaining a structure using a peristaltic pump, and 3) a lyophilized or hydrated decellularized nerve graft that can be stored even at room temperature may be manufactured. In addition, 4) the decellularization process and the decellularization process for nervous tissue may be performed for a shorter time than before.

In the present invention, after b), washing of the decellularized nerve graft may be further performed. As the washing solution, distilled water may be used.

In one embodiment, the washing may be performed in a peristaltic pump system.

In addition, in the present invention, after b), lyophilizing the decellularized nerve graft may be further performed. Through lyophilization, moisture in the decellularized nerve graft may be removed.

In one embodiment, the moisture content in the decellularized nerve graft after lyophilization may be 10% or less, or 1% to 8%.

In addition, in the present invention, sterilizing the decellularized nerve graft may be further performed.

In one embodiment, sterilization may be performed by irradiation, and the irradiation range may range from 10 to 30 kGy.

In one embodiment, in the case of the decellularized nerve graft provided in a hydrated form, it may be manufactured by being sterilized after washing.

In addition, in the case of the decellularized nerve graft provided in a lyophilized form, the washed decellularized nerve graft is lyophilized in a cryopreservation solution and then sterilized, thereby manufacturing the lyophilized nerve graft. Here, the cryopreservation solution may be any cryopreservation solution used in the art without limitation, and for example, maltitol may be used.

In addition, the present invention relates to a decellularized nerve graft manufactured by the method of manufacturing a decellularized nerve graft described above.

In the decellularized nerve graft manufactured by the manufacturing method according to the present invention, the structure of nervous tissue is maintained in a state in which lipid and cells are removed. The decellularized nerve graft has the advantage that it can be stored frozen or stored in a lyophilized or hydrated form, which can be stored even at room temperature.

The decellularized nerve graft can be transplanted into a peripheral nerve-damaged patient.

The present invention will be described in further detail regarding the following examples. However, the scope of the present invention is not limited to the following examples, and it will be understood by those of ordinary skill in the art that various modifications, alterations, or applications are possible without departing from the technical details derived from the details described in the accompanying claims.

EXAMPLES

Example 1

Manufacture of Decellularized Nerve Graft

Decellularized nerve grafts were manufactured by the following process using allogeneic nervous tissues collected from a cadaver donated from a tissue bank for non-profit patient treatment.

a) A lipid was detached from the nervous tissue using forceps.

b) To remove a lipid that was not detached, delipidation was carried out for 2 to 16 hours using a mixed solution containing 40% to 60% isopropyl alcohol and 40% to 60% hexane.

c) Cells were removed by treating the lipid-removed nervous tissue with NaOH and then SDC (manufacture of decellularized nerve graft). The treatment concentration and treatment time are shown in Table 1 below.

d) To wash the residue from the nervous tissue from which lipids and cells have been removed (decellularized nerve graft), the tissue was washed with sterile distilled water for 30 minutes, and the washing procedure was repeated 4 to 8 times.

e) The b) to d) processes were performed at 50 to 300 rpm using a peristaltic pump (Jenie Well, JWCP-600) system of FIG. 1. In addition, the solution was sent to a waste water storage bin in the d) process (washing procedure) using a three-way stopcock and circulated in the b) process of delipidation and the c) process of removing cells using a basic solution and a surfactant to reduce the use of the solutions.

f) In the case of a hydrated nerve graft, the washed decellularized nerve graft was sterilized by 15 kGy irradiation.

g) In the case of a lyophilized nerve graft, the washed decellularized nerve graft was immersed in a cryopreservation solution, maltitol, and then lyophilized to have a moisture content of 10% or less, and preferably 1% to 8%. In addition, the final lyophilized product was sterilized by 15 kGy irradiation.

Experimental Example 1

Confirmation of Residual Cells and Structure of Decellularized Nerve Graft by Manufacturing Condition To confirm the optimal conditions for the process of manufacturing a decellularized nerve graft, residual cells and structures of decellularized nerve grafts manufactured by the treatment with various concentrations of NaOH and SDC and various times were confirmed.

Specifically, decellularized nerve grafts were manufactured by the manufacturing method of Example 1 (however, manufactured using a shaker), and here, the concentration and treatment time of NaOH and SDC are shown in Table 1.

TABLE 1

| | Decellularization solution (concentration) | | |
|---|---|---|---|
| Sample | NaOH | SDC | Treatment time |
| 1 | 4N to 8N | X | 4 to 18 hours |
| 2 | X | 5% to 16% | 4 to 8 hours |
| 3 | 0.1N to 2N | — | 1 to 2 hours |
| | — | 2% to 4% | 1 to 2 hours |

In addition, to confirm the residual cells and structures of the manufactured decellularized nerve grafts, 4',6-diamidino-2-phenylindole (DAPI) staining and scanning electron microscopy (SEM) were performed. The results are shown in FIG. 2A.

In addition, DNA quantification was performed, and the result is shown in FIG. 2B.

As shown in FIG. 2, it can be confirmed that when NaOH and SDC are used alone, cells or proteins in the tissue are not completely removed.

When NaOH and SDC are used together (Sample 3), high decellularization efficiency may be achieved with a lower concentration and a shorter time, compared to when NaOH and SDC are used alone (Sample 1 and Sample 2, respectively). In addition, Sample 3 showed a lower amount of residual DNA than other samples, which was measured to be less than the reference value of 50 ng/mg. That is, it can be confirmed that the decellularization method according to the present invention has a higher decellularization effect.

However, it was confirmed that Samples 1 to 3 using a shaker do not have uniform structures.

Experimental Example 2

Optimal Condition Setting for Decellularization Nerve Graft

When both NaOH and SDC were used as a decellularization solution according to Experimental Example 1, it was confirmed that cells were removed better than when NaOH and SDC were used alone, and the DNA content was less than the reference value of 50 ng/mg.

However, since the structure inside the tissue is not uniform, to improve this, the process was performed using a peristaltic pump, unlike the conventional case in which cells were removed using a shaker.

Specifically, a decellularized nerve graft was manufactured by the manufacturing method of Example 1 using a peristaltic pump, and a decellularized nerve graft manufactured using a shaker was used as a comparative example. Here, the treatment concentration and treatment time for the decellularization solution are the same as those for Sample 3 of Experimental Example 1.

TABLE 2

| | Shaker | Peristaltic Pump |
|---|---|---|
| Process time | 84 hr | 36 hr |

Table 2 shows the entire process time (that is, the time for delipidation, decellularization, and washing) according to the use of a shaker and a peristaltic pump. As shown in Table 2, when the peristaltic pump is used, compared to when the shaker is used, it can be confirmed that the processing time is reduced by 50% or more.

Meanwhile, to confirm the residual cells and structure of the manufactured decellularized nerve graft, DAPI staining and SEM imaging were performed, and the results are shown in FIG. 3A. In addition, DNA quantification was performed, and the result is shown in FIG. 3B.

In addition, in this experimental example, to confirm tissue uniformity, in each SEM image, the volume of each pore was measured, and the distribution of pores by volume was confirmed compared to the total number of pores. The result is shown in FIG. 3C.

As shown in FIG. 3, it was confirmed that, when the shaker was used, the structure in the tissue is not uniform, and cells or other proteins in the tissue are lower than but close to the reference value of 50 ng/mg. However, it can be confirmed that, when the pump was used, cells or other proteins remaining in tissue were completely removed, and the DNA amount was decreased by 50% or more compared to when the shaker was used.

Furthermore, the process using the shaker took approximately 3 days, but when the pump was used, the process took approximately 2 days. In terms of the tissue structure, it was confirmed that, when the shaker was used, the pore size was not uniform, but when the pump was used, most pores have a uniform size of 10 to 20 μm.

Experimental Example 3

Verification of Delipidation, Decellularization, and Structure Maintenance Abilities of Decellularized Nerve Graft To verify the delipidation, decellularization, and structure maintenance abilities of the decellularized nerve graft manufactured in Example 1, the decellularization process according to the present invention and the decellularization process according to the conventional processes (Sondell and Hudson) were performed.

1(1) Verification of Delipidation Ability of the Present Process Compared to the Conventional Process The decellularized nerve graft manufactured by the process of Example 1 was used as an experimental group, and the decellularized nerve grafts manufactured according to the conventional processes were as controls. To verify the delipidation ability, Oil Red O staining was performed.

The result is shown in FIG. 4.

As shown in FIG. 4, as a result of the Oil Red O staining, in the conventional process, a lipid remaining in a raw material was not completely removed and thus stained, whereas no staining was observed in the decellularized nerve graft manufactured in the example. That is, when the manufacturing method according to the present invention is used, it can be confirmed that lipid was completely removed.

(2) Verification of Decellularization Ability of the Present Process Compared to the Conventional Process The decellularized nerve graft manufactured by the process of Example 1 was used as an experimental group, and the decellularized nerve grafts manufactured by the conventional processes were used as controls. To verify the degree of decellularization of the manufactured grafts, DAPI staining and H&E staining were performed, and to quantify residual DNA, DNA content was measured by Nano Drop.

The result is shown in FIG. 5.

As shown in FIG. 5, as a result of the DAPI staining and H&E staining, unlike when cells were not completely removed by the conventional processes, it can be confirmed that there were no residual cells in the decellularized nerve graft manufactured by the process of the Example 1 (FIGS. 5A and 5B). In addition, as a result of DNA quantification, it can be confirmed that the decellularized nerve graft manufactured in Example 1 exhibited better decellularization ability as the residual DNA amount was decreased to the reference value of 50 ng/mg or less.

(3) Verification of Structure Maintenance Ability of the Present Process Compared to the Conventional Process The decellularized nerve graft manufactured by the process of Example 1 was used as an experimental group, and the decellularized nerve grafts manufactured according to the conventional processes were as controls. To verify the structure maintenance ability of the manufactured grafts, structural analysis was performed through SEM imaging.

The result is shown in FIG. 5D.

As shown in FIG. 5D, as a result of confirming the tissue structure, it can be confirmed that the structure is not maintained and collapses in the case of the conventional processes, whereas the structure is maintained without collapsing in the case of the decellularized nerve graft manufactured in Example 1.

Example 2

Manufacture of Various Forms of Decellularized Nerve Grafts

The decellularized nerve graft manufactured in Example 1 was prepared in lyophilized and hydrated forms and observed with the naked eye, and then photographed by SEM.

The result is shown in FIG. 6.

As shown in FIG. 6, it can be confirmed that the structures were maintained without collapsing even when the decellularized nerve graft was lyophilized and then rehydrated. That is, the decellularized nerve graft manufactured according to the present invention may be provided in a lyophilized or hydrated form that can be stored even at room temperature.

INDUSTRIAL AVAILABILITY

In addition, unlike a conventional product distributed in a frozen state, a lyophilized or hydrated decellularized nerve graft that can be stored at room temperature may be provided.

The invention claimed is:

1. A method of manufacturing a decellularized nerve graft, comprising:

providing a nervous tissue;

a) removing a lipid component of the nervous tissue, thereby providing lipid component- removed nervous tissue; and b) removing cells from the lipid component-removed nervous tissue, wherein:

b) is performed by treating the lipid component-removed nervous tissue with a basic solution that comprises one or more bases and is free of an anionic surfactant, and then with a separate anionic surfactant solution that comprises one or more anionic surfactants and is free of the one or more bases;

in b), the time for treatment with the basic solution is 30 minutes to 9 hours, and the time for treatment with the anionic surfactant solution is 30 minutes to 9 hours; and a) and b) are performed using a peristaltic pump system operated at 50 to 300 rpm (revolutions per minute);

the one or more bases is selected from the group consisting of sodium hydroxide, potassium hydroxide, ammonium hydroxide, calcium carbonate, magnesium hydroxide, calcium hydroxide, and ammonia;

the one or more anionic surfactants is selected from the group consisting of sodium deoxycholate (SDC), sodium dodecyl sulfate (SDS), alkylbenzene sulfonate (ALS), alcohol ether sulfates (AES), sodium lauryl sulfate (SLS), and polyethylene glycol (PEG); and the concentration of the one or more bases in the basic solution is 0.1 to 8N (normal concentration).

2. The method of claim 1, wherein, a) is performed using a delipidation solution, wherein the delipidation solution includes a polar solvent, a non-polar solvent, or a mixed solvent thereof.

3. The method of claim 1, wherein the one or more bases is sodium hydroxide, and the one or more anionic surfactants is sodium deoxycholate (SDC).

4. The method of claim 1, wherein the concentration of the one or more bases in the basic solution is 0.1 to 1 N (normal concentration).

5. The method of claim 1, wherein the peristaltic pump system comprises a peristaltic pump;

a chamber connected with the peristaltic pump that contains the nervous tissue;

a reservoir connected with the peristaltic pump that stores a treatment liquid for treating the nervous tissue; and a waste water storage bin connected with the chamber where the treatment liquid that has been used for treating the nervous tissue is discharged.

6. The method of claim 5, wherein the treatment liquid used for treating the nervous tissue is recycled and reused.

7. The method of claim 1, wherein the method further comprises:

washing the decellularized nerve graft, wherein the washing is performed in the peristaltic pump system.

8. The method of claim 1, wherein the method further comprises:

lyophilizing and sterilizing the decellularized nerve graft.

9. A decellularized nerve graft manufactured by the preparation method of claim 1, wherein the decellularized nerve graft has a uniform pore size of 10 to 20 μm.

* * * * *